United States Patent
Kajikawa et al.

[11] Patent Number: 6,103,785
[45] Date of Patent: Aug. 15, 2000

[54] WATER-ABSORBING AGENT AND ITS PRODUCTION PROCESS AND USE

[75] Inventors: Katsuhiro Kajikawa; Kinya Nagasuna, both of Himeji, Japan

[73] Assignee: Nippon Shokubai Co., Ltd., Osaka, Japan

[21] Appl. No.: 09/275,071

[22] Filed: Mar. 23, 1999

[30] Foreign Application Priority Data

Mar. 26, 1998 [JP] Japan .................................. 10-100671

[51] Int. Cl.⁷ .................................................. C08K 7/02
[52] U.S. Cl. ............................................................ 523/220
[58] Field of Search ............................................. 523/220

[56] References Cited

U.S. PATENT DOCUMENTS

| | | |
|---|---|---|
| 4,727,097 | 2/1988 | Kobayashi et al. . |
| 5,382,610 | 1/1995 | Harada et al. . |
| 5,422,406 | 6/1995 | Yang et al. . |
| 5,731,365 | 3/1998 | Engelhardt et al. . |

FOREIGN PATENT DOCUMENTS

| | | |
|---|---|---|
| 0 493 011 | 7/1992 | European Pat. Off. . |
| 0 605 150 | 7/1994 | European Pat. Off. . |
| 0 703 265 | 3/1996 | European Pat. Off. . |
| 0 819 721 | 1/1998 | European Pat. Off. . |
| 56-159232 | 12/1981 | Japan . |
| 60-36534 | 2/1985 | Japan . |
| 61-257235 | 11/1986 | Japan . |
| 62-036411 | 2/1987 | Japan . |
| 5-31362 | 2/1993 | Japan . |
| 05070762 | 3/1993 | Japan . |
| 5-506263 | 9/1993 | Japan . |
| 5-507511 | 10/1993 | Japan . |
| 6-184320 | 7/1994 | Japan . |
| 8-84927 | 4/1996 | Japan . |
| 9-278900 | 10/1997 | Japan . |
| 91/15368 | 10/1991 | WIPO . |
| 91/18042 | 11/1991 | WIPO . |

*Primary Examiner*—Kriellion Sanders

[57] ABSTRACT

The present invention provides: a water-absorbing agent which has high absorption capacity, fast absorption speed, and excellent liquid permeability; and a production process and a use for such a water-absorbing agent. A water-absorbent fine particle having a lower absorption capacity than a water-absorbent resin particle is fixed to the surface of the water-absorbent resin particle, or portions having a higher crosslinking density than internal portions are discontinuously present in the neighborhood of the surface of the water-absorbent resin particle. In addition, the water-absorbing agent is produced using a water-absorbent crosslinking agent which is swellable in itself.

25 Claims, 2 Drawing Sheets

WATER-ABSORBING AGENT AND ITS PRODUCTION PROCESS AND USE

BACKGROUND OF THE INVENTION

A. Technical Field

The present invention relates to a water-absorbing agent and its production process and use, more particularly, a water-absorbing agent and its production process and an absorbent article wherein the water-absorbing agent is favorably used not only for sanitary materials such as disposable diapers, sanitary napkins, and incontinent pads, but also in various industrial fields such as public works, agriculture, and horticulture.

B. Background Art

In recent years, water-absorbing agents comprising water-absorbent resins are widely utilized in fields, for example, of sanitary materials, such as disposable diapers, sanitary napkins, and so-called incontinent pads, for the purpose of causing the water-absorbent resins to absorb body fluids.

Known examples of the above water-absorbent resins are as follows: crosslinked polymers of partially neutralized polyacrylic acids; hydrolyzed products of starch-acrylonitrile graft polymers; neutralized products of starch-acrylic acid graft polymers; saponified products of vinyl acetate-acrylic acid ester copolymers; hydrolyzed products of acrylonitrile- or acrylamide copolymers, and their crosslinked polymers; and crosslinked polymers of cationic monomers.

Examples of the properties which the above water-absorbing agents should have are excellent properties such as absorption capacity or speed and liquid-permeability upon contact with aqueous liquids such as body fluids. However, relations between these properties do not necessarily display positive correlations. For example, as the absorption capacity increases, properties such as liquid-permeability or absorption speed deteriorate.

As to a method for improving such water-absorption properties of the water-absorbing agent in good balance, there is a proposed art in which the neighborhood of the surface of the water-absorbent resin is crosslinked with crosslinking agents such as polyhydric alcohols. In addition, there are also known methods in which when the crosslinking agent is added the following materials are allowed to be present as third substances, thus attempting to more uniformly distribute the crosslinking agent on the surface of the water-absorbent resin to uniformly carry out the surface-crosslinking in the course of the above crosslinking reaction: inert inorganic powders; dihydric alcohols; ether compounds; water-soluble polymers; and alkylene oxide adducts of monohydric alcohols, or organic acid salts, or lactams (for example, JP-A-56-159232, JP-A-60-036534, JP-A62-036411, JP-A-05-031362, JP-A-05-507511, JP-A-06-184320, JP-A-08-084927).

However, because most of crosslinking agents or treatment solutions containing them, as actually used, are liquid compounds, they have high affinity for the water-absorbent resin, and their reaction or absorption to the resin starts simultaneously with their mixing with the resin, so it is difficult to uniformly disperse them onto the surface of the water-absorbent resin or to uniformly produce a surface-crosslinked layer, and it is also impossible to freely control the extent of the crosslinking in the surface neighborhood. In addition, the above conventional surface-crosslinking may be able to prevent the liquid permeability from depressing, but still deteriorates the absorption capacity. In addition, there are reported methods in which inorganic powders or powdered denaturing agents (as obtained by powdering of denaturing agents such as liquid crosslinking agents) are attached to the surface of water-absorbent resin particles (JP-A-61-257235, JP-A-09-278900), or crosslinkages between water-absorbent resin particles are formed with crosslinking agents, thereby granulating and aggregating the resin particles. These methods may also improve the liquid permeability, but are still insufficient in respect to the improvement of the absorption properties.

SUMMARY OF THE INVENTION

A. Object of the Invention

An object of the present invention is to provide: a water-absorbing agent which is excellent in the absorption capacity, the absorption speed, and the liquid permeability with good balance; and a production process and a use for such a water-absorbing agent; wherein neither conventional liquid surface-crosslinking agents nor treatment solutions containing them are used.

B. Disclosure of the Invention

The present inventors diligently studied to solve the above problems. As a result, they found that if a water-absorbent fine particle having a lower absorption capacity than a water-absorbent resin particle is fixed to the surface of the water-absorbent resin particle, then the fine particle of the small swelling extent gets to exist on the surface of the water-absorbent resin particle, so that what is called gel blocking, which is caused by the shape change of the water-absorbent resin particle when it swells, can be prevented to ensure the liquid permeability. Furthermore, the present inventors found that such a method can prevent the absorption capacity from depressing and can easily control the absorption capacity of final products even if a plurality of the fine particle is present on the surface of the water-absorbent resin particle, because the fine particle on the surface also has water absorbency to some extent. Thus, the inventors completed the present invention.

That is to say, a water-absorbing agent, according to the present invention, is characterized by comprising a water-absorbent resin particle and a water-absorbent fine particle, wherein the water-absorbent fine particle has a lower absorption capacity than the water-absorbent resin particle and is fixed to the surface of the water-absorbent resin particle.

In addition, if the above water-absorbing agent according to the present invention is regarded from another viewpoint, namely, from the crosslinking density distribution of the water-absorbent resin particle surface, then the water-absorbing agent according to the present invention is characterized by comprising a water-absorbent resin particle in which portions having a higher crosslinking density than internal portions are discontinuously present in the neighborhood of the surface.

In addition, a production process for a water-absorbing agent, according to the present invention, involves the use of a crosslinking agent and is characterized in that the crosslinking agent is a water-absorbent crosslinking agent which is swellable in itself.

Furthermore, an absorbent article, according to the present invention, is characterized by comprising the above present invention water-absorbing agent or a water-absorbing agent that is obtained by the above present invention production process.

These and other objects and the advantages of the present invention will be more fully apparent from the following detailed disclosure.

DETAILED DESCRIPTION OF THE INVENTION (Form of water-absorbing agent):

In the present invention, the form of the fixing of the water-absorbent fine particle is not especially limited, and it may be the form in which the entirety of the water-absorbent fine particle is either gotten into the water-absorbent resin particle from its surface and therefore embedded in the water-absorbent resin particle, or gotten out of the water-absorbent resin particle. In a particularly preferable form, at least part of the water-absorbent fine particle is embedded in the surface of the water-absorbent resin particle in a state where the water-absorbent fine particle partially projects from the surface of the water-absorbent resin particle. The above passage "the water-absorbent fine particle is embedded in the surface of the water-absorbent resin particle in a state where the water-absorbent fine particle partially projects from the surface of the water-absorbent resin particle" means a state where a portion (e.g. about $\frac{1}{3}$~about $\frac{1}{10}$ of the diameter) of the water-absorbent fine particle is gotten into the water-absorbent resin particle from its surface, and the rest (e.g. about $\frac{2}{3}$~about $\frac{9}{10}$ of the diameter) is gotten out of the surface of the water-absorbent resin particle. In the case where the entirety of the water-absorbent fine particle is gotten into the water-absorbent resin particle and therefore embedded in the resin particle, the water-absorbent fine particle might hardly function as the surface-crosslinked layer. In addition, also in the case where the entirety of the water-absorbent fine particle is gotten out of the water-absorbent resin particle, the bonding between the water-absorbent fine particle and the water-absorbent resin particle is so weak that the water-absorbent fine particle might hardly function as the surface-crosslinked layer.

As to the present invention water-absorbing agent, the water-absorbent fine particle as fixed to the surface of the water-absorbent resin particle needs to have a lower absorption capacity than the water-absorbent resin particle, wherein the absorption capacity of the water-absorbent fine particle is preferably 80% or less of that of the water-absorbent resin particle. The absorption capacity is, for example, evaluated using deionized water, wherein the absorption capacity for deionized water of the water-absorbent fine particle, as fixed to the surface of the water-absorbent resin particle, is preferably in the range of 1.5~100 g/g, and it is more preferable that the absorption capacity for deionized water of the water-absorbent resin particle is 200 g/g or more, and that the absorption capacity for deionized water of the water-absorbent fine particle, as fixed to the surface of the water-absorbent resin particle, is in the range of 1.5~100 g/g. The absorption capacity for deionized water, as referred to herein, is defined in the below-mentioned "DETAILED DESCRIPTION OF THE PREFERRED EMBODIMENTS" portion hereof and, generally, may be said to be absorption capacity for pure water.

Therefore, the most preferable water-absorbing agent in the present invention comprises a water-absorbent resin particle and a water-absorbent fine particle, wherein the water-absorbent resin particle has an absorption capacity of 200 g/g or more for deionized water, and the water-absorbent fine particle has an absorption capacity of 1.5~100 g/g for deionized water and is fixed to the surface of the water-absorbent resin particle by being embedded in the surface of the water-absorbent resin particle in a state where the water-absorbent fine particle partially projects from the surface of the water-absorbent resin particle. The absorption capacity for deionized water of the water-absorbent fine particle is more preferably in the range of 3~50 g/g. In the cases where the absorption capacity for deionized water of the water-absorbent fine particle is too large and too small, the surface-crosslinking effect by the fine particle is difficult to obtain, and the improvement of the absorption speed or liquid permeability is little.

In the present invention, the water-absorbent fine particle may be merely physically fixed to the surface of the water-absorbent resin particle, but it is preferable that a chemical bond is formed between the water-absorbent fine particle and the water-absorbent resin particle. Among chemical bonds, the covalent bond is preferred to the ionic bond, because the covalent bond is stronger than the ionic bond. Specifically, it is preferable that the water-absorbent fine particle has a functional group, more preferably, at least two functional groups, such as hydroxyl group, carboxyl group, or amino group, reactable upon a functional group (for example, acid group such as carboxyl group) of the surface of the water-absorbent resin particle (the above water-absorbent fine particle having at least two functional groups might hereinafter be referred to as water-absorbent crosslinking agent), because a covalent bond is formed by a reaction between the functional groups (preferably, and further the surface neighborhood of the water-absorbent resin particle is crosslinked with the above water-absorbent crosslinking agent) to strengthen the bonding between the fine particle and the water-absorbent resin particle.

The average particle diameter of the water-absorbent fine particle is preferably at most $\frac{1}{10}$, more preferably in the range of $\frac{1}{20}$~$\frac{1}{1,000}$, of that of the water-absorbent resin particle. In the case where the average particle diameter of the fine particle is too large, the state of the fine particle is near to the granulation of the water-absorbent resin particle rather than the state where the fine particle is fixed to the water-absorbent resin particle or embedded in the water-absorbent resin particle such that the fine particle partially projects from the water-absorbent resin particle, so it might be difficult that the fine particle displays the function of the surface-crosslinked layer that the present invention aims at. In addition, the lower limit of the average particle diameter of the water-absorbent fine particle is not especially limited, but it is regarded as practically sufficient that the average particle diameter of the fine particle is 0.01 $\mu$m or more, or $\frac{1}{10,000}$ or more of that of the water-absorbent resin particle in view of the balance between the cost and the effects of the present invention, because it is difficult to produce a water-absorbent fine particle with an average particle diameter less than 0.01 $\mu$m by a simple process at a low cost. Specifically, it is preferable that the average particle diameter of the water-absorbent resin particle is in the range of 100~600 $\mu$m, and that the average particle diameter of the water-absorbent fine particle is in the range of 0.01~50 $\mu$m.

In addition, if the above water-absorbing agent according to the present invention is regarded from another viewpoint, namely, from the crosslinking density distribution of the water-absorbent resin particle surface, then the water-absorbing agent according to the present invention is characterized by comprising a water-absorbent resin particle in which portions having a higher crosslinking density than internal portions are discontinuously present in the neighborhood of the surface. The discontinuous presence of portions, having a higher crosslinking density than internal portions, in the neighborhood of the surface gives the same effects as above, namely, not only can prevent the absorption capacity from depressing, but also can ensure the liquid permeability.

(Water-absorbent fine particle):

The water-absorbent fine particle in the present invention is a fine particle with a specific absorption capacity, and a particularly preferably usable one comprises a water-absorbent resin as obtained by polymerizing a water-soluble, ethylenically unsaturated monomer and crosslinking the resultant product in high density. The aimed fine particle with low absorption capacity can be obtained by controlling the crosslinking density, because the absorption capacity decreases as the crosslinking density increases.

Preferable examples of the water-absorbent fine particle include water-absorbent resins with reactive functional groups such as amide, hydroxyl, amino, imino, epoxy, isocyanate, carbonate, oxazoline, haloepoxy, silanol, aldehyde, sulfonic acid, and carboxyl groups, and particularly preferable ones are those which have hydroxyl, amino, epoxy, and carbonate groups. In addition, more preferable examples of the water-absorbent fine particle further include a polymer as obtained by radical polymerization of a monomer mixture including (a) an $\alpha,\beta$-ethylenically unsaturated monomer containing a hydroxyl group, (b) an $\alpha,\beta$-ethylenically unsaturated monomer containing a carboxyl group, and (c) an $\alpha,\beta$-ethylenically unsaturated monomer containing a carboxylic acid salt group. Such a polymer is generally obtainable by polymerizing the below-mentioned monomer and crosslinking the resultant product in high density.

Examples of the monomer, as used to produce the water-absorbent fine particle, include: anionic unsaturated monomers, such as (meth)acrylic acid, ethacrylic acid, crotonic acid, sorbic acid, maleic acid, itaconic acid, cinnamic acid, their anhydrides, vinylsulfonic acid, allylsulfonic acid, styrenesulfonic acid, vinyltoluenesulfonic acid, 2-(meth)acrylamido-2-methylpropanesulfonic acid, 2-(meth)acryloylethanesulfonic acid, 2-(meth)acryloylpropanesulfonic acid, 2-hydroxyethylacryloyl phosphate, 2-hydroxyethylmethacryloyl phosphate, phenyl-2-acryloyloxyethyl phosphate, and vinylphosphoric acid, and their salts; nonionic unsaturated monomers containing a hydrophilic group, such as acrylamide, methacrylamide, N-ethyl (meth)acryl amide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, N-vinylpyrrolidone, N-acryloylpiperidine, and N-acryloylpyrrolidine; cationic unsaturated monomers such as N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide, alkyleneamines, vinylamine, allylamine, N-vinylimidazole, vinylpyridine, vinylpyridineamine oxide, ethylenimine, and their quaternary salts; allyl alcohol; hydroxyalkyl esters of vinylcarboxylic acid monomers, such as 2-hydroxyethyl (meth)acrylate, 2-hydroxypropyl (meth)acrylate, 3-hydroxypropyl (meth)acrylate, and 4-hydroxybutyl (meth)acrylate; di- or trialkylene glycol mono(meth)acrylates such as diethylene glycol mono(meth)acrylate, triethylene glycol mono(meth)acrylate, dipropylene glycol mono(meth)acrylate, and tripropylene glycol mono(meth)acrylate; polyalkylene glycol mono(meth)acrylates (wherein the number of the repeating alkylene units is 4~50); mono(meth)acrylates of polyhydric alcohols, such as glycerol mono(meth)acrylate, neopentyl glycol mono (meth)acrylate, and pentaerythritol mono (meth)acrylate; and glycidyl-group-containing monomers such as glycidyl acrylate and glycidyl methacrylate.

These may be used either alone respectively or in combinations with each other. In addition, also available are monomers, such as vinyl alcohol, which cannot exist alone, but can form hydroxyl groups by polymerizing vinyl acetate and then saponifying the resultant polymer.

If the effects of the present invention are not damaged, other $\alpha,\beta$-ethylenically unsaturated monomers which are copolymerizable with the above monomers may be used as additional components of the monomer mixture to produce the water-absorbent fine particle.

In addition, in a preferable process, a crosslinking agent having at least two unsaturated or reactive groups per molecule is added to the monomer mixture to produce the water-absorbent fine particle, thus crosslinking the monomer mixture in high density simultaneously with its polymerization. Examples of such a crosslinking agent include: ethylene glycol di(meth)acrylate, diethylene glycol di(meth)acrylate, triethylene glycol di(meth)acrylate, polyethylene glycol di(meth)acrylate, polypropylene glycol di(meth)acrylate, glycerol di(meth)acrylate, glycerol tri(meth)acrylate, trimethylolpropane di(meth)acrylate, trimethylolpropane tri(meth)acrylate, neopentyl glycol di(meth)acrylate, N,N'-methylenebismethacrylamide, tetraallyloxyethane, triallylamine, ethylene glycol, propylene glycol, glycerol, ethylene glycol diglycidyl ether, ethylene carbonate, and polyethylenimine. The use of such a crosslinking agent can shorten the heating treatment time to react the water-absorbent crosslinking agent and the water-absorbent resin particle and therefore can prevent the deterioration of the resin as caused by heating at high temperature for a long time, and further, can lower the tackiness of the surface of the resultant gelatinous polymer to thereby improve the handling property. The amount of the crosslinkable monomer as used is in the range of preferably 0.001~0.5 mol %, more preferably 0.01~0.3 mol %, of the monomer mixture.

As to methods for the radical polymerization of the above monomer mixture, polymerization methods as conventionally employed for the polymerization of the water-absorbent resin, such as aqueous solution polymerization, reversed-phase suspension polymerization, and emulsion polymerization, are usable with no modification. When or after being dried, the resultant polymer is heated at a temperature of the material of preferably 60~250° C., more preferably 150~250° C., for preferably 10 minutes~20 hours, more preferably 10 minutes~10 hours, to react functional groups in the molecule of the above polymer upon each other, whereby a polymer of low absorption capacity can be obtained. The aimed water-absorbent fine particle can be obtained by pulverizing and classifying this polymer if necessary.

As to other processes to obtain the water-absorbent fine particle, there are for example the following processes: a process in which, when a partially neutralized acrylic acid is polymerized, a large quantity of polyhydric alcohols, polyglycidyl compounds, polyaziridine compounds, polyamines, polyisocyanates, glyoxal, alkylene carbonates, or silane coupling agents are used as crosslinking agents, and the heating is carried out at higher temperature for a longer time than usual; and a process involving the use of a large quantity of crosslinkable monomer having at least two unsaturated groups per molecule. In addition, a process, comprising the steps of reacting a polymer (which is obtained by polymerizing the above monomer), for example, a water-soluble polymer such as polyacrylic acid (or salts thereof) or polyethylenimine, upon a crosslinking agent and pulverizing and classifying the resultant product, can also be exemplified as the process to obtain the water-absorbent fine particle in the present invention.

(Water-absorbent resin particle):

The water-absorbent resin particle, usable in the present invention, can be a conventionally known water-absorbent resin and is therefore not especially limited, but what has an acid group is preferable, and a water-absorbent crosslinkable polymer containing a carboxyl group can be exemplified as such. A typical example thereof is obtainable by polymerizing hydrophilic monomers of which the main component is either one or both of acrylic acid and a salt thereof. Examples of such a water-absorbent resin include: crosslinked polymers of partially neutralized polyacrylic acids (U.S. Pat. No. 4,625,001, U.S. Pat. No. 4,654,039, U.S. Pat. No. 5,250,640, U.S. Pat. No. 5,275,773, and EP 456136), crosslinked and partially neutralized starch-acrylic acid graft polymers (U.S. Pat. No. 4,076,663), isobutylene-maleic acid copolymers (U.S. Pat. No. 4,389,513), saponified products of vinyl acetate-acrylic acid copolymers (U.S. Pat. No. 4,124,748), hydrolyzed products of acrylamide (co)polymers (U.S. Pat. No. 3,959,569), and hydrolyzed products of acrylonitrile polymers (U.S. Pat. No. 3,935,099). Particularly, the crosslinked polymer of partially neutralized polyacrylic acid is preferable. It is preferable that 50~90 mol % of the acid group in the crosslinked polymer of partially neutralized polyacrylic acid is neutralized. Examples of the salt include alkaline metal salts, ammonium salts, and amine salts. The crosslinked polymer of partially neutralized polyacrylic add may be what is obtained by copolymerizing the above acrylic acid or its salt (preferably used as the main component of the monomers) with other monomers, if necessary. Specified examples of the above other monomers include: anionic unsaturated monomers, such as acrylic acid, methacrylic add, ethacrylic acid, crotonic acid, sorbic acid, maleic acid, itaconic acid, cinnamic acid, their anhydrides, vinylsulfonic acid, allylsulfonic acid, styrenesulfonic acid, vinyltoluenesulfonic acid, 2-(meth)acrylamido-2-methylpropanesulfonic acid, 2-(meth)acryloylethanesulfonic acid, 2-(meth)acryloylpropanesulfonic acid, 2-hydroxyethylacryloyl phosphate, 2-hydroxyethylmethacryloyl phosphate, phenyl-2-acryloyloxyethyl phosphate, and vinylphosphoric acid, and their salts; nonionic unsaturated monomers containing a hydrophilic group, such as acrylamide, methacrylamide, N-ethyl(meth)acrylamide, N-n-propyl(meth)acrylamide, N-isopropyl(meth)acrylamide, N,N-dimethyl(meth) acrylamide, 2-hydroxyethyl (meth)acrylate, 2-hydroxypropyl (meth)acrylate, methoxypolyethylene glycol (meth)acrylate, polyethylene glycol mono(meth) acrylate, N-vinylpyrrolidone, N-acryloylpiperidine, and N-acryloylpyrrolidine; cationic unsaturated monomers such as N,N-dimethylaminoethyl (meth)acrylate, N,N-diethylaminoethyl (meth)acrylate, N,N-dimethylaminopropyl (meth )acrylate, N,N-dimethylaminopropyl(meth)acrylamide, alkyleneamines, vinylamine, allylamine, N-vinylimidazole, vinylpyridine, vinylpyridineamine oxide, ethylenimine, and their quaternary salts. The amount of these other monomers than acrylic acid, as used, is usually in the range of preferably 0~50 mol % (but not including 50 mol %), more preferably 0~30 mol %, of the entire monomers.

Examples of the crosslinked structure of the water-absorbent resin particle, usable in the present invention, include: self-crosslinking types using no crosslinking agent; and copolymerized or reacted types with an internal-crosslinking agent having two or more polymerizable unsaturated groups or two or more reactive groups. A preferable one is the water-absorbent resin particle having the crosslinked structure as copolymerized or reacted with the internal-crosslinking agent.

Specified examples of the above internal-crosslinking agent include: N,N-methylenebis(meth)acrylamide, (poly) ethylene glycol di(meth)acrylate, (poly)propylene glycol di(meth)acrylate, trimethylolpropane tri(meth)acrylate, trimethylolpropane di(meth)acrylate, glycerol tri(meth) acrylate, glycerol acrylate methacrylate, ethylene-oxide-denatured trimethylolpropane tri(meth)acrylate, pentaerythritol tetra(meth)acrylate, dipentaerythritol hexa (meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, polyethylenimine, and glycidyl (meth)acrylate. In addition, these internal-crosslinking agents may be used in combinations with each other. Particularly, it is preferable to essentially use a compound with two or more polymerizable unsaturated groups as the internal-crosslinking agent, considering the water absorption properties of the resultant water-absorbent resin particle. The amount of the above internal-crosslinking agent as used is in the range of preferably 0.005~3 mol %, more preferably 0.01~1.5 mol %, of the above monomer components.

Incidentally, in the polymerization, the following materials may be added: hydrophilic polymers such as starch, cellulose, their derivatives, polyvinyl alcohol, polyacrylic acid (or its salts), and crosslinked polymers of polyacrylic acid (or its salts); and chain transfer agents such as hypophosphorous acid (or its salts).

When the above monomer (of which the main component is, for example, acrylic acid or a salt thereof) is polymerized to obtain the water-absorbent resin particle as used in the present invention, bulk polymerization or precipitation polymerization can be carried out. However, considering the performance or the easiness of the polymerization control, it is preferable to carry out aqueous solution polymerization or reversed-phase suspension polymerization using the above monomer in the form of its aqueous solution. Such polymerization methods are conventionally known in public and are, for example, disclosed in U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683,274, U.S. Pat. No. 4,690,996, U.S. Pat. No. 4,721,647, U.S. Pat. No. 4,738,867, U.S. Pat. No. 4,748,076.

When the above polymerization is carried out, the following, for example, can be used: radical polymerization initiators such as potassium persulfate, ammonium persulfate, sodium persulfate, t-butyl hydroperoxide, hydrogen peroxide, and 2,2'-azobis(2-amidinopropane) dihydrochloride; active energy rays such as ultraviolet rays and electron beam. In addition, in the case where oxidizable radical polymerization initiators are used, they may be combined with reductants, such as sodium sulfite, sodium hydrogensulfite, ferrous sulfate, and L-ascorbic acid, to carry out redox polymerization. The amount of the above polymerization initiator as used is in the range of usually 0.001~2 mol %, preferably 0.01~0.5 mol %.

As to the shape of the water-absorbent resin as obtained by the above polymerization, various ones are available for the present invention, and examples thereof are irregular by pulverization, spherical, fibrous, bar-shaped, approximately spherical, or flat. The average particle diameter of the water-absorbent resin is in the range of preferably 200~600

μm, and the content therein of particles of 150 μm or below is preferably at most 10%, more preferably at most 5%.
(Production process for water-absorbing agent):

The production process for a water-absorbing agent, according to the present invention, involves the use of a crosslinking agent and is characterized in that the crosslinking agent is a water-absorbent crosslinking agent which is swellable in itself. As is aforementioned, the water-absorbent crosslinking agent, as referred to in the present invention, is a water-absorbent fine particle having at least two functional groups (for example, hydroxyl group, carboxyl group, or amino group) reactable upon a functional group (for example, add group such as carboxyl group) of the surface of the water-absorbent resin particle.

As is aforementioned, if the water-absorbent crosslinking agent is used, either one or both of a covalent bond and an ionic bond are preferably formed by a reaction between a functional group of the surface of the water-absorbent resin particle and a functional group of the water-absorbent crosslinking agent, whereby the surface of the water-absorbent resin particle is crosslinked with the above water-absorbent crosslinking agent, so that the bonding between the fine particle and the water-absorbent resin particle is strengthened.

The water-absorbent crosslinking agent, as used in the above present invention production process for a water-absorbing agent, preferably has a latent absorption capacity of 1.5~100 g/g for deionized water. The latent absorption capacity for deionized water, as referred to herein, is defined in the below-mentioned "DETAILED DESCRIPTION OF THE PREFERRED EMBODIMENTS" portion hereof. Furthermore, the latent absorption capacity for deionized water of the water-absorbent crosslinking agent is more preferably in the range of 3~50 g/g. In the cases where the latent absorption capacity for deionized water of the water-absorbent crosslinking agent is too large and too small, the surface-crosslinking effect by the water-absorbent crosslinking agent is difficult to obtain, and the improvement of the absorption speed or liquid permeability is little.

In addition, it is regarded as practically sufficient that the average particle diameter of the water-absorbent crosslinking agent is 0.01 μm or more, or 1/10,000 or more of that of the water-absorbent resin particle in view of the balance between the cost and the effects of the present invention, because it is difficult to produce a water-absorbent crosslinking agent with an average particle diameter less than 0.01 μm by a simple process at a low cost. Specifically, the average particle diameter of the water-absorbent crosslinking agent, as used in the above present invention production process for a water-absorbing agent, is in the range of preferably 0.01~50 μm and more preferably 0.1~10 μm.

The water-absorbent crosslinking agent, as used in the present invention production process for a water-absorbing agent, is preferably an organic powder that can absorb a specific amount of deionized water. A particularly preferably usable one comprises a fine particle of a water-absorbent resin as obtained by polymerizing the aforementioned water-soluble, ethylenically unsaturated monomer and crosslinking the resultant product in high density. The aimed fine particle. with low absorption capacity can be obtained by controlling the crosslinking density, because the absorption capacity decreases as the crosslinking density increases.

A preferably usable method therefor comprises the steps of mixing the water-absorbent resin particle with the above water-absorbent crosslinking agent and an aqueous liquid and heating the resultant mixture. That is to say, if the water-absorbent crosslinking agent is used in the form of the mixture with the aqueous liquid, the surface of the water-absorbent resin particle falls in so to speak a plasticized state, so that it becomes easy to fix the water-absorbent crosslinking agent to the surface of the water-absorbent resin particle or to embed the water-absorbent crosslinking agent into the surface of the water-absorbent resin particle such that the water-absorbent crosslinking agent will partially project from the surface of the water-absorbent resin particle. Furthermore, the heating treatment preferably causes a reaction between a functional group of the surface of the water-absorbent resin particle and a functional group of the water-absorbent crosslinking agent to form either one or both of a covalent bond and an ionic bond, so that the bonding between the water-absorbent crosslinking agent and the water-absorbent resin particle becomes strong.

The amount of the water-absorbent crosslinking agent is in the range of preferably 1~50 weight parts, more preferably 5~20 weight parts, per 100 weight parts of the water-absorbent resin. In the case where the amount of the water-absorbent crosslinking agent is too small, the aimed formation of the surface-crosslinked layer might be insufficient. On the other hand, in the case where the amount of the water-absorbent crosslinking agent is too large, the water absorption capacity of the water-absorbent crosslinking agent itself might be low, so that the water absorption capacity of the water-absorbing agent might become depressed.

The above aqueous liquid may be either water alone or a mixed liquid of water and a hydrophilic organic solvent miscible therewith. Examples of the hydrophilic organic solvent include methanol, ethanol, isopropanol, butanol, ethylene glycol monomethyl ether, ethylene glycol monoethyl ether, propylene glycol monomethyl ether, tetrahydrofuran, dimethylformamide, dimethyl sulfoxide, acetone, and methyl ethyl ketone. Particularly, ethanol and isopropanol are preferable. The amount of the aqueous liquid as used is in the range of preferably 10~100 weight parts, more preferably 20~80 weight parts, per 100 weight parts of the water-absorbent resin particle.

Conventional dryers or heating-furnaces are available for the heating treatment Examples thereof include channel type stirring dryers, rotary dryers, disk dryers, fluidized-bed dryers, gas-stream dryers, and infrared dryers. In this case, the heating treatment temperature is in the range of preferably 40~250° C., more preferably 90~230° C., still more preferably 120~220° C. In the case where the heating treatment temperature is lower than 40° C., the suction amount might be depressed. On the other hand, in the case where the heating treatment temperature is higher than 250° C., there is a danger that the thermal deterioration will occur according to the type of the water-absorbent resin as used. The heating treatment time is usually in the range of preferably 1~120 minutes, more preferably 10~60 minutes.

Incidentally, if the effects of the present invention are not damaged, before and/or after the treatment with the above water-absorbent crosslinking agent in the present invention, the surface-crosslinking may be carried out by conventional surface-crosslinking methods.
(Absorbent article):

The absorbent article according to the present invention comprises an absorbent layer which includes the present invention water-absorbing agent and is interposed between a sheet with liquid permeability and a sheet with liquid impermeability. Then, because the above absorbent article has the absorbent layer including the present invention water-absorbing agent, this absorbent article has the above-mentioned excellent absorption properties. Specified examples of the absorbent article include sanitary materials such as disposable diapers, sanitary napkins, and so-called incontinence pads, and is not especially limited. However, particularly preferable examples thereof include disposable diapers and sanitary napkins. Because the absorbent article has excellent absorption properties, it can prevent urine from leaking and can afford so-called dry feeling in the case where the absorbent article is, for example, a disposable diaper.

The above-mentioned sheet with liquid permeability (hereinafter referred to as liquid-permeable sheet) comprises a material that is permeable with aqueous liquids. Examples of the material forming the liquid-permeable sheet include: nonwoven fabrics, woven fabrics; porous synthetic resin films of polyethylene, polypropylene, polyester, polyamide. In addition, the above-mentioned sheet with liquid impermeability (hereinafter referred to as liquid-impermeable sheet) comprises a material that is impermeable with aqueous liquids. Examples of the material forming the liquid-impermeable sheet include: synthetic resin films of polyethylene, polypropylene, ethylene vinyl acetate, polyvinyl chloride; films of combined materials of these synthetic resins with nonwoven fabrics; films of combined materials of the above-mentioned synthetic resins with woven fabrics. Incidentally, the liquid-impermeable sheet may be permeable with vapor.

The constitution of the absorbent layer is not especially limited if it has the present invention water-absorbing agent. In addition, the process for producing the absorbent layer is not especially limited. Furthermore, the method for interposing the absorbent layer between the liquid-permeable sheet and the liquid-impermeable sheet, namely, the process for producing the absorbent article, is not especially limited.

Incidentally, it is permissible to give various functions to the above water-absorbing agent or absorbent article by further adding materials, such as deodorants, antimicrobial agents, perfumes, various inorganic powders, foaming agents, pigments, dyes, hydrophilic short fibers, manure, oxidants, reductants, water, and salts, to the water-absorbing agent.

(Effects and Advantages of the Invention):

The present invention can give a water-absorbing agent which has high absorption capacity, fast absorption speed, and excellent liquid permeability.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to these examples.

In the examples, unless otherwise noted, the unit "part(s)" is by weight.

The performances of the water-absorbing agent were measured by the following methods:

(a) Absorption capacity:

First, 0.2 g of sample resin or water-absorbent fine particle was uniformly placed into a nonwoven-fabric-made tea bag type bag (40×150 mm) and then immersed into a 0.9 wt % aqueous sodium chloride solution (physiological salt solution) or deionized water (pure water). Sixty minutes later, the bag was drawn up and then left in the air for 5 seconds and then drained with a cleaning tissue for 10 seconds, and the resultant weight $W_1$ (g) of the bag was then measured. The same procedure was carried out using neither sample resin nor water-absorbent fine particle, and the resultant weight was measured as the blank weight $W_0$ (g). Thus, the absorption capacity (g/g) was calculated from these $W_1$ and $W_0$ in accordance with the following equation:

$$\text{absorption capacity (g/g)} = \frac{\text{weight } W_1(g) - \text{weight } W_0(g)}{\text{weight (g) of sample resin or water-absorbent fine particle}}$$

(b) Latent absorption capacity:

A process, preferably usable to produce the water-absorbing agent, comprises the steps of mixing the water-absorbent resin particle with the water-absorbent crosslinking agent and an aqueous liquid and heating the resultant mixture. The absorption capacity of the water-absorbent crosslinking agent, as displayed after the treatment of the water-absorbent crosslinking agent under the same heating treatment conditions as those for the above process except the absence of the water-absorbent resin particle, is referred to as the latent absorption capacity, and the measurement method therefor is in accordance with the above measurement method for the absorption capacity of the water-absorbent fine particle.

Figure 1:
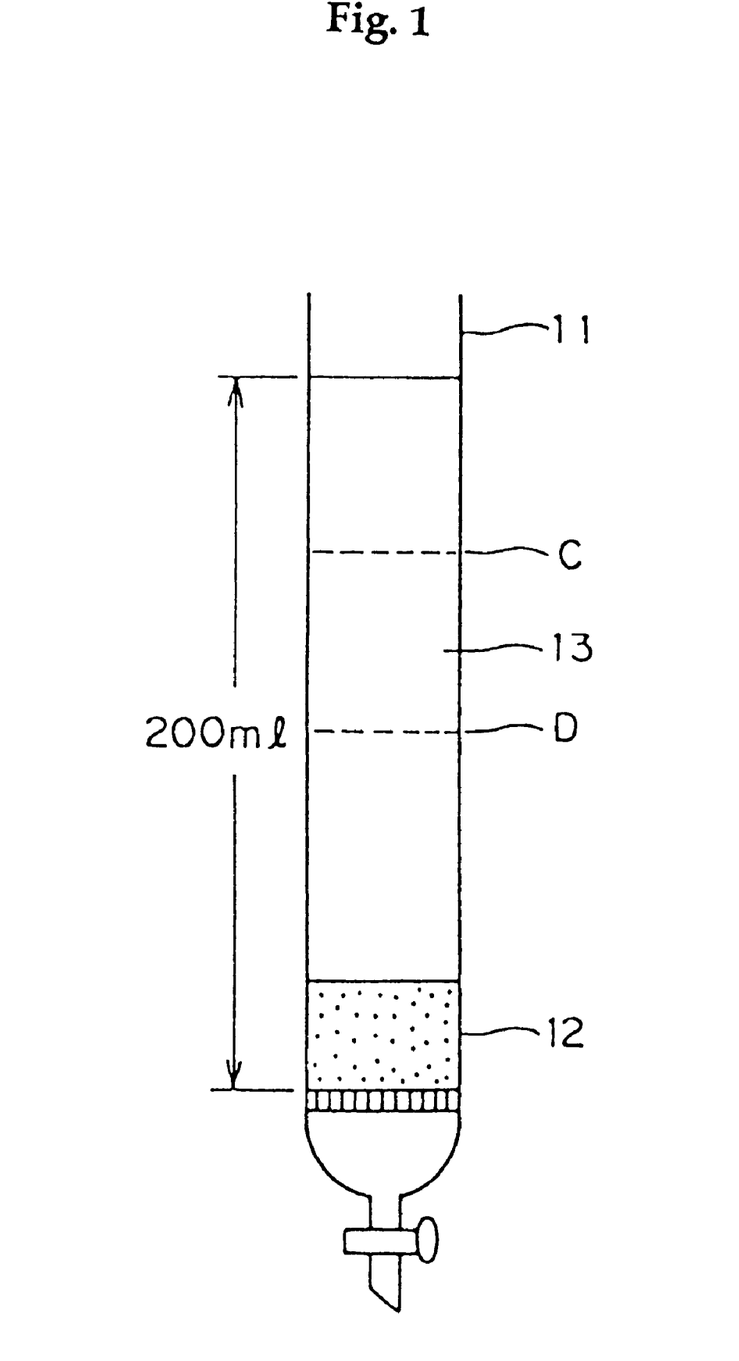
FIG. 1 is a figure for illustrating the measurement method of the liquid permeability in the examples of some preferred embodiments.

(c) Liquid permeability:

First of all, 0.5 g of sample resin was filled into a glass column 11 with a cock ("Biocolumn CF-30K" made by Iuchi Seieido Co., Ltd., catalog code 22-635-07, lower part filter #G2, inner diameter =1 inch, length =400 mm) as shown in FIG. 1, and the sample resin was then swollen in equilibrium with an excess of physiological salt solution (in about 1 hour). Next, after the swollen sample resin 12 had settled sufficiently, the meniscus was set to the liquid level of 200 ml, and the cock was then opened. Then, the residence time of the physiological salt solution 13 in the range (liquid amount =50 ml as measured) between two standard lines C (meniscus of 150 ml in liquid level) and D (meniscus of 100 ml in liquid level) was measured, and the average value of the three-time measurements was regarded as the liquid permeability (unit: second).

Incidentally, the value, as measured with the above apparatus in the absence of the sample resin, was 10 seconds.

(d) Absorption speed:

First of all, 0.358 g of sample resin (classification product of 300~850 $\mu$n) was spread into a glass-made test tube (height: 126 mm) of about 14.1 $\mu$m in inner diameter. Next, 10.0 g of artificial urine (1), of which the temperature was set at 25° C., was gently poured onto the sample resin at once to measure the number of the seconds in time which passed until it was seen with the eye that the 10 g of artificial urine was entirely absorbed by the 0.358 g of sample resin to form a 28-time (g/g) swollen gel. Then, the value, as given by dividing the 28 times (g/g) by the measured number of the seconds, was regarded as the absorption speed (g/g/second). The larger this value is, the higher the absorption speed is. The above artificial urine (1) is an aqueous solution containing sodium sulfate, potassium chloride, magnesium chloride hexahydrate, calcium chloride dihydrate, ammonium dihydrogenphosphate, and diammonium hydrogenphosphate in the concentrations of 0.2 weight %, 0.2 weight %, 0.05 weight %, 0.025 weight %, 0.085 weight %, and 0.015 weight % respectively in a dissolved state.

(e) Suction amount:

About 1 g of sample resin was added onto 16ply toilet paper (55 mm×75 mm) as immersed in 20 ml of artificial urine (2) in a Petri dish of 95 mm in inner diameter, thus allowing the sample resin to absorb the liquid for 5 minutes. Then, the resultant swollen gel was separated, and its weight was measured. The measured weight of the swollen gel, as absorbed the liquid, was divided by the original weight of the sample resin to calculate the suction amount (g/g) of the sample resin. The above artificial urine (2) is an aqueous solution containing urea, sodium chloride, magnesium sulfate, and calcium chloride in the concentrations of 1.9 weight %, 0.8 weight %, 0.1 weight %, and 0.1 weight % respectively in a dissolved state.

EXAMPLE 1

A reaction solution to produce a water-absorbent resin particle was prepared by dissolving 2.72 parts of trimethylolpropane triacrylate (as the internal-crosslinking agent) into 4,400 parts of a 37 weight % aqueous solution of sodium acrylate (neutralization ratio: 75 mol %) (as the monomer component). Next, this reaction solution was degassed under a nitrogen gas atmosphere for 30 minutes.

Then, the reaction solution was supplied into a reaction vessel as prepared by capping a stainless-steel-made double-arm type kneader having two sigma type wings and a jacket. While maintaining the reaction solution at 30° C., the atmosphere inside the above reaction vessel was replaced with a nitrogen gas. Next, while the reaction solution was stirred, 1.1 parts of sodium persulfate (as the polymerization initiator) and 1.1 parts of sodium sulfite (as the reductant to promote the decomposition of the polymerization initiator) were added to the reaction solution, so that a polymerization reaction got started about 1 minute after. The polymerization was carried out at 30–80° C., and the resultant hydrogel polymer was got out 40 minutes after the initiation of the polymerization.

The resultant hydrogel polymer was spread on a wire net and dried at 150° C. with hot air for 2 hours. Then, the resultant dried product was pulverized with a hammer mill and further classified with a wire net of 850 μm in mesh size, thus obtaining water-absorbent resin particle (1) with an average particle diameter of 400 μm and an absorption capacity of 330 g/g for deionized water.

A reaction solution to produce a water-absorbent fine particle was prepared as 1,200 parts of an aqueous solution of monomer components (monomer concentration: 37 weight %) comprising sodium acrylate 67.5 mol %, acrylic acid 22.5 mol %, hydroxyethyl acrylate 9.95 mol %, and N,N'-methylenebisacrylamide 0.05 mol %. Next, this reaction solution was degassed under a nitrogen gas atmosphere for 30 minutes. Then, the reaction solution was supplied into a reaction vessel as prepared by capping a stainless-steel-made double-arm type kneader having two sigma type wings and a jacket. While maintaining the reaction solution at 35° C., the atmosphere inside the above reaction vessel was replaced with a nitrogen gas. Next, while the reaction solution was stirred, 0.5 parts of sodium persulfate (as the polymerization initiator) and 0.5 parts of sodium sulfite (as the reductant to promote the decomposition of the polymerization initiator) were added to the reaction solution, so that a polymerization reaction got started about 5 minute after. The polymerization was carried out at 30–80° C., and the resultant hydrogel polymer was got out 60 minutes after the initiation of the polymerization.

The resultant hydrogel polymer was spread on a wire net and dried at 100° C. with hot air for 2 hours. Then, the resultant dried product was pulverized with a jet mill and then heated at 180° C. in a wind-free dryer for 3 hours, thus obtaining water-absorbent fine particle (1) with an average particle diameter of 25 μm, an absorption capacity of 4.8 g/g for deionized water, and a latent absorption capacity of 3.6 g/g for deionized water.

Five parts of water-absorbent fine particle (1) above was added to 100 parts of water-absorbent resin particle (1) above to mix them, and the resultant mixture was further mixed with an aqueous liquid (comprising 20 parts of water and 20 parts of isopropyl alcohol) for about 5 minutes using Lödige Mixer (M5R, made by Gebrüder Lödige Maschinenbau GmbH). The resultant mixture was put into a drying machine and then heated at 200° C. for 1 hour, thus obtaining water-absorbing agent (1) according to the present invention.

EXAMPLE 2

Water-absorbing agent (2) according to the present invention was obtained in the same way as of Example 1 except that the amount of water-absorbent fine particle (1) was changed to 10 parts.

EXAMPLE 3

Water-absorbent fine particle (2) with an average particle diameter of 27 μm was obtained in the same way as the production steps for water-absorbent fine particle of Example 1 except that the composition of the monomer components was as follows: sodium acrylate 60 mol %, acrylic acid 20 mol %, hydroxyethyl acrylate 20 mol %. As to water-absorbent fine particle (2), the absorption capacity for deionized water was 2.5 g/g, and the latent absorption capacity for deionized water was 2.3 g/g.

Ten parts of water-absorbent fine particle (2) above was added to 100 parts of water-absorbent resin particle (1) above to mix them, and the resultant mixture was further mixed with an aqueous liquid (comprising 20 parts of water and 40 parts of isopropyl alcohol) for about 5 minutes using Lödige Mixer (M5R, made by Gebrüder Lödige Maschinenbau GmbH). The resultant mixture was put into a drying machine and then heated at 200° C. for 2 hour, thus obtaining water-absorbing agent (3) according to the present invention.

EXAMPLE 4

Water-absorbing agent (4) according to the present invention was obtained in the same way as of Example 3 except that the amount of water-absorbent fine particle (2) was changed to 15 parts.

EXAMPLE 5

A reaction solution to produce a water-absorbent fine particle was prepared as 76 parts of an aqueous solution of monomer components (monomer concentration: 35 weight %) comprising sodium acrylate 71.25 mol %, acrylic acid 23.75 mol %, and diethylene glycol diglycidyl ether 5.0 mol %. Next, this reaction solution was degassed with nitrogen. Separately therefrom, 2 parts of sorbitan monostearate was dissolved into 195 parts of cyclohexane at 40° C. and degassed. The above reaction solution was put into a separable flask and degassed with nitrogen again, and 0.06 part of sodium persulfate was then added thereto under highspeed stirring. Furthermore, the above cyclohexane solution was dropped thereto under stirring, on the way of which a phase transition occurred. The bath temperature was raised in such a state to carry out polymerization at about 65° C. The aging was carried out for 1 hour since the end of the dropping. After the aging, the bath temperature was raised to 80° C. to azeotropically distil off water, thus adjusting the solid content of the resultant polymer gel to 50 weight %. The resultant hydrogel was filtered off by suction.

The resultant hydrogel was dried at 150° C. with a hot air for 2 hours, thus obtaining water-absorbent fine particle (3) with an average particle diameter of 10 μm, an absorption capacity of 46 g/g for deionized water, and a latent absorption capacity of 38 g/g for deionized water.

Next, 0.2 part of water-absorbent fine particle (3) above was added to 100 parts of water-absorbent resin particle (1) (as obtained in Example 1) to mix them, and the resultant mixture was further mixed with an aqueous liquid (comprising 20 parts of water and 0.1 part of isopropyl alcohol) for about 5 minutes using Lödige Mixer (M5R, made by Gebrüder Lödige Maschinenbau GmbH). The resultant mixture was put into a drying machine and then heated at 180° C. for 30 minutes, thus obtaining water-absorbing agent (5) according to the present invention.

Figure 2:
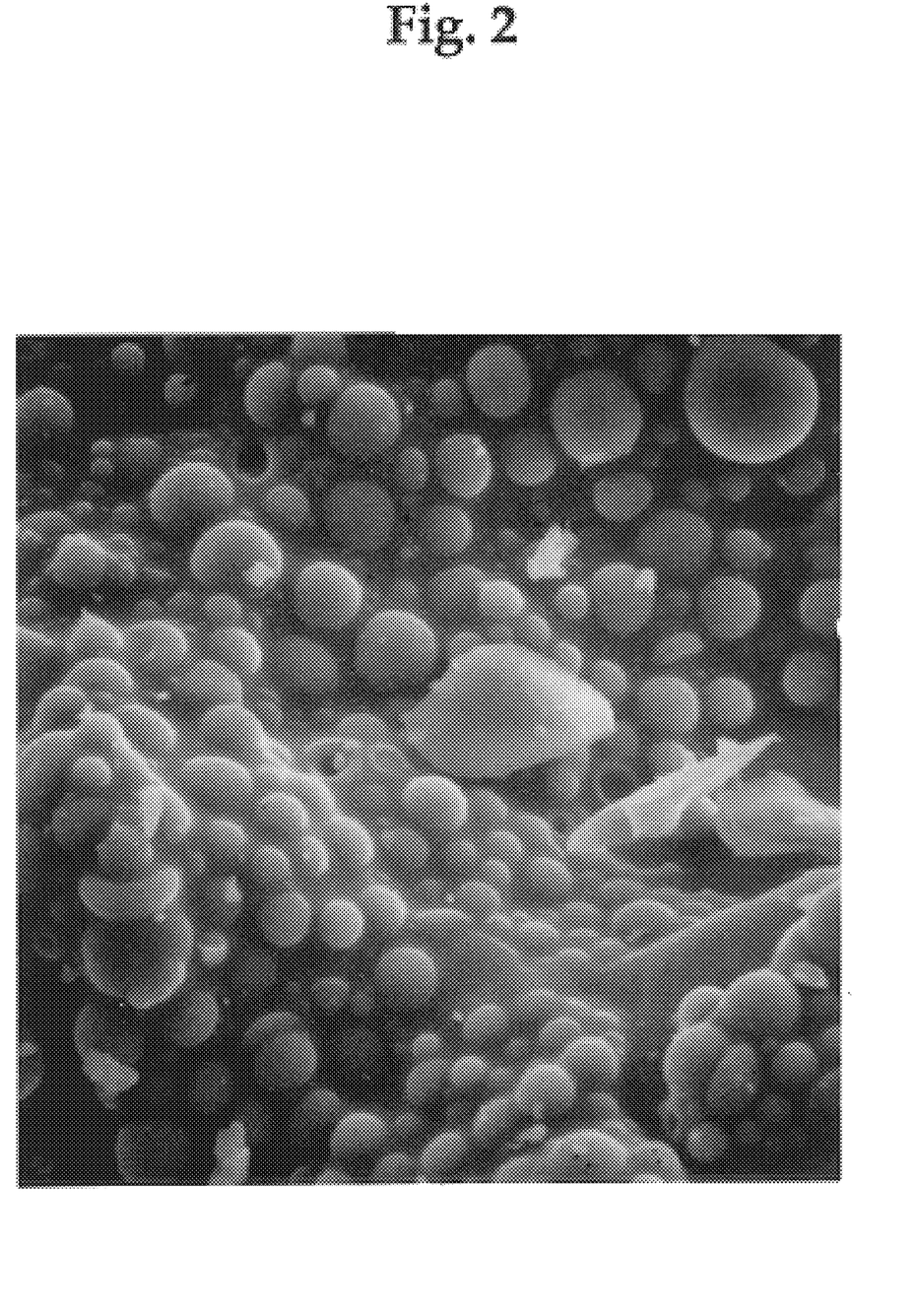
FIG. 2 is a magnified schematic view showing the surface state of water-absorbing agent (5) (as obtained in Example 5).

Water-absorbing agent (5) was observed with an electron microscope. As a result, it was confirmed that the water-absorbent fine particle was embedded in the water-absorbent resin particle in a state where the water-absorbent fine particle partially projected from the water-absorbent resin particle, specifically, at the deepest about ⅓ and at the most shallow about ¹⁄₁₀ of the diameter of the water-absorbent fine particle was embedded in the water-absorbent resin particle. This is shown in FIG. 2.

COMPARATIVE EXAMPLE 1

Water absorbent resin particle (1), as obtained in Example 1, was referred to as comparative water-absorbing agent (1).

COMPARATIVE EXAMPLE 2

First, 100 parts of water-absorbent resin particle (1), as obtained in Example 1, was mixed with an aqueous liquid (comprising 0.5 part of glycerol, 2 parts of water, and 0.5 part of isopropyl alcohol) for about 30 minutes using Lödige Mixer (M5R, made by Gebrüder Lödige Maschinenbau GmbH). The resultant mixture was put into a drying machine and then heated at 180° C. for 1 hour, thus obtaining comparative water-absorbing agent (2).

COMPARATIVE EXAMPLE 3

Comparative water-absorbing agent (3) was obtained in the same way as of Comparative Example 2 except that the heating temperature of the mixture was changed to 200° C.

The absorption capacity, the liquid permeability, the absorption speed, and the suction amount were measured for water-absorbing agents (1)~(5) and comparative water-absorbing agents (1)~(3) as obtained above. The results are shown in Table 1.

TABLE 1

| | | Absorption capacity (g/g) | Absorption speed (g/g/second) | Suction amount (g/g) | Liquid permeability (second) |
|---|---|---|---|---|---|
| Example 1 | Water-absorbing agent (1) | 48 | 0.60 | 16.0 | 120 |
| Example 2 | Water-absorbing agent (2) | 46 | 0.76 | 16.5 | 110 |
| Example 3 | Water-absorbing agent (3) | 46 | 0.78 | 16.6 | 105 |

TABLE 1-continued

| | | Absorption capacity (g/g) | Absorption speed (g/g/second) | Suction amount (g/g) | Liquid permeability (second) |
|---|---|---|---|---|---|
| Example 4 | Water-absorbing agent (4) | 45 | 0.65 | 15.6 | 90 |
| Example 5 | Water-absorbing agent (5) | 46 | 0.50 | 15.2 | 110 |
| Comparative Exampe 1 | Comparative water-absorbing agent (1) | 48 | 0.02 | 8.2 | 230 |
| Comparative Example 2 | Comparative water-absorbing agent (2) | 40 | 0.16 | 15.5 | 160 |
| Comparative Example 3 | Comparative water-absorbing agent (3) | 35 | 0.25 | 15.6 | 130 |

Comparative water-absorbing agents (2) and (3) (as obtained by surface-crosslinking the water-absorbent resin particle of Comparative Example 1 with glycerol) are improved in respect to the absorption speed, the suction amount, and the liquid permeability, but are deteriorated in respect to the absorption capacity, when compared with the water-absorbent resin particle of Comparative Example 1. In contrast therewith, water-absorbing agents (1)~(5) (in which the water-absorbent fine particle of low absorption capacity is fixed or embedded in a state where the water-absorbent fine particle partially projects) are more greatly improved in respect to the absorption speed, the suction amount, and the liquid permeability than comparative water-absorbing agents (2) and (3), because water-absorbing agents (1)~(5) have a uniform surface-crosslinked layer. Furthermore, almost no depression of the absorption capacity is seen with regard to water-absorbing agents (1)~(5), because the water-absorbent fine particle hardly soaks into the water-absorbent resin particle.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A water-absorbing agent, comprising a water-absorbent resin particle and a water-absorbent fine particle, wherein the water-absorbent fine particle has a lower absorption capacity than the water-absorbent resin particle and is fixed to the surface of the water-absorbent resin particle.

2. A water-absorbing agent according to claim 1, wherein the fixing is made by embedding at least part of the water-absorbent fine particle into the surface of the water-absorbent resin particle such that at least part of the water-absorbent fine particle will partially project from the surface of the water-absorbent resin particle.

3. A water-absorbing agent according to claim 1, wherein the fixing is accomplished by forming a chemical bond between the water-absorbent fine particle and the water-absorbent resin particle.

4. A water-absorbing agent according to claim 3, wherein the chemical bond is a covalent bond.

5. A water-absorbing agent according to claim 1, wherein the absorption capacity of the water-absorbent fine particle is 80 % or less of that of the water-absorbent resin particle.

6. A water-absorbing agent according to claim 1, wherein the absorption capacity of the water-absorbent fine particle is in the range of 1.5~100 g/g for deionized water.

7. A water-absorbing agent according to claim 6, wherein the absorption capacity of the water-absorbent resin particle is 200 g/g or more for deionized water.

8. A water-absorbing agent according to claim 1, wherein the average particle diameter of the water-absorbent fine particle is 1/10 or less of that of the water-absorbent resin particle.

9. A water-absorbing agent according to claim 1, wherein the average particle diameter of the water-absorbent resin particle is in the range of 100~600 μm, and the average particle diameter of the water-absorbent fine particle is in the range of 0.01~50 μm.

10. A water-absorbing agent according to claim 1, wherein the water-absorbent fine particle is an organic powder.

11. A water-absorbing agent, comprising a water-absorbent resin particle in which portions having a higher crosslinking density than internal portions are discontinuously present in the neighborhood of the surface.

12. A production process for a water-absorbing agent, involving the use of a crosslinking agent, being characterized in that the crosslinking agent is a water-absorbent crosslinking agent which is swellable in itself.

13. A production process according to claim 12, comprising the step of treating the surface of a water-absorbent resin with the water-absorbent crosslinking agent.

14. A production process according to claim 12, wherein the water-absorbent crosslinking agent has a latent absorption capacity of 1.5~100 g/g for deionized water.

15. A production process according to claim 12, wherein the water-absorbent crosslinking agent has an average particle diameter of 0.01~50 μm.

16. A production process according to claim 12, wherein the water-absorbent crosslinking agent is an organic powder.

17. An absorbent article, comprising the water-absorbing agent as recited in claim 1.

18. An absorbent article according to claim 17, which is a disposable diaper.

19. An absorbent article according to claim 17, which is a sanitary napkin.

20. An absorbent article, comprising the water-absorbing agent as recited in claim 11.

21. An absorbent article according to claim 20, which is a disposable diaper.

22. An absorbent article according to claim 20, which is a sanitary napkin.

23. An absorbent article, comprising a water-absorbing agent that is obtained by a production process as recited in claim 12.

24. An absorbent article according to claim 23, which is a disposable diaper.

25. An absorbent article according to claim 23, which is a sanitary napkin.

* * * * *